United States Patent [19]
Acharya et al.

[11] Patent Number: 5,646,304
[45] Date of Patent: Jul. 8, 1997

[54] PROCESS FOR THE PRODUCTION OF PETROCHEMICALS

[75] Inventors: Divyanshu R. Acharya, Bridgewater; Satish S. Tamhankar, Scotch Plains, both of N.J.

[73] Assignee: The BOC Group, Inc., New Providence, N.J.

[21] Appl. No.: 494,293

[22] Filed: Jun. 23, 1995

[51] Int. Cl.$^6$ .................................................. C07D 307/60
[52] U.S. Cl. ...................... 549/259; 549/256; 549/257; 549/258; 549/260; 558/320; 568/575; 570/224
[58] Field of Search ...................................... 549/256, 257, 549/258, 259, 260, 533; 558/320; 568/575; 570/224

[56] References Cited

U.S. PATENT DOCUMENTS

| | | | |
|---|---|---|---|
| 4,231,943 | 11/1980 | Paradis et al. | 549/259 |
| 4,987,239 | 1/1991 | Ramachandran et al. | 549/250 |
| 5,126,463 | 6/1992 | Ramachandran et al. | 549/262 |
| 5,262,547 | 11/1993 | Ramachandran et al. | 549/262 |

FOREIGN PATENT DOCUMENTS 2544972  4/1977  Germany.

*Primary Examiner*—Bernard Dentz
*Attorney, Agent, or Firm*—Coleman R. Reap; Salvatore P. Pace

[57] ABSTRACT

A petrochemical is produced by the vapor phase reaction of a hydrocarbon with air in the presence of a suitable catalyst. The petrochemical is removed from the reactor effluent, and part or all of the remaining petrochemical-free gas stream is passed through a hydrocarbon-selective adsorbent, which adsorbs hydrocarbon from the gas stream, leaving a hydrocarbon-depleted waste gas. Hydrocarbon is purged from the adsorbent with air, and the air-hydrocarbon mixture is recycled to the partial oxidation reactor. The purge air, and preferably both the purge air and the petrochemical-free gas stream are dried by passage through beds of zeolite 3A prior to being introduced into the hydrocarbon-selective adsorbent, and the beds of zeolite 3A are regenerated by passing heated hydrocarbon-depleted waste gas therethrough.

19 Claims, 6 Drawing Sheets

PROCESS FOR THE PRODUCTION OF PETROCHEMICALS

FIELD OF THE INVENTION

The present invention is directed to a process for producing petrochemicals from a hydrocarbon and an oxygen-containing gas in the presence of a suitable catalyst, and more particularly to a hydrocarbon partial oxidation process in which unreacted hydrocarbon separated from other components of a gaseous waste stream is recycled to the partial oxidation reactor.

BACKGROUND OF THE INVENTION

Certain petrochemicals are produced commercially by the partial oxidation of an appropriate hydrocarbon in the vapor phase over a suitable catalyst and in the presence of an oxygen-containing gas. For example, cyclic anhydrides are produced commercially by the vapor phase catalytic partial oxidation of aromatic hydrocarbons, such as o-xylene or benzene, or straight-chain hydrocarbons, such as n-butane, or butene, in the presence of an oxygen-containing gas, over a vanadium-containing catalyst. Similarly, nitriles, alkylene oxides, aldehydes and halogenated hydrocarbons are produced by the partial oxidation of appropriate alkanes and alkenes in the presence of selected catalysts. Air is generally used as the oxygen-containing gas, because of its low cost and ready availability. The reaction can be carried out in any suitable reactor, such as a fixed bed, fluidized bed, moving bed, trickle bed or transport bed reactor, and it produces the petrochemical, and generally carbon monoxide (CO), carbon dioxide ($CO_2$), water, and smaller amounts of other partially oxidized by-products. The reaction equipment train generally consists of a reactor, in which the petrochemical product is produced, a scrubber, in which the petrochemical product is scrubbed from the reactor effluent gases by means of water or other solvent for the petrochemical, and means for further treating the scrubbed effluent gases.

Currently, it is common to practice the above-described process on a single pass basis with the conversion of hydrocarbon to the desired petrochemical product being maximized. This results in a low overall efficiency, since the selectivity to petrochemical product is below the maximum. Consequently, the scrubber effluent gas contains considerable amounts of CO and $CO_2$, in addition to unreacted hydrocarbon. These products are usually incinerated, so that the only return realized from them is heat value. In many instances the products are flared, so that even the heat value is not realized. In modified processes, a portion of the scrubber effluent gas is recycled, the conversion of the hydrocarbon feedstock is lowered and the selectivity of hydrocarbon conversion to the desired petrochemical product is increased. The remainder of the effluent is purged from the system to prevent the build-up of CO, $CO_2$ and nitrogen (introduced into the system when air is used as the source of oxygen). These improvements result in a reduced "per pass" conversion, but the overall efficiency of the process is increased.

Federal Republic of Germany (FRG) Patent Application Disclosure 25 44 972 discloses a maleic anhydride manufacturing process in which the reactor feed comprises $C_4$ hydrocarbons, air, CO and $CO_2$. In the process of this patent, maleic anhydride is recovered from the reactor effluent gas stream and a portion of the remaining stream is recycled to the reactor. This patent also teaches recovering butane by temperature swing adsorption (TSA) from the non-recycled gas stream and recycling the recovered butane to the reactor. The butane is desorbed from the adsorbent at elevated temperature by fresh air, and the air-butane mixture is recycled to the reactor.

U.S. Pat. No. 4,231,943 discloses the production of maleic anhydride by the reaction of n-butane and air in the presence of a catalyst comprising vanadium and phosphorus oxides. The process of this patent includes the steps of recovering maleic anhydride from the gaseous oxidation reactor effluent, directly recycling a portion of the maleic anhydride-free effluent to the reactor, separating relatively pure n-butane from the remaining gaseous effluent and recycling the relatively pure n-butane to the feed stream.

U.S. Pat. No. 4,987,239 discloses a process for the production of anhydrides by the partial oxidation reaction of a hydrocarbon with an oxygen-containing gas in the presence of a suitable catalyst. In the process of this patent, the gaseous effluent from the maleic anhydride product scrubber is compressed and sent to a selective separator, e.g. a pressure swing adsorption (PSA) unit containing a hydrocarbon-selective adsorbent, wherein a substantial proportion of the unreacted hydrocarbon contained in the effluent is recovered, and the unreacted hydrocarbon and a controlled amount of a gaseous flame suppressor is recycled to the partial oxidation reactor.

The above patents do not discuss or make allowance for moisture contained in the gaseous effluent from the partial oxidation product recovery unit and in purge air. Moisture is produced in the partial oxidation reaction; accordingly, the hot gaseous effluent from the reactor contains moisture. As the effluent gas passes through the product scrubber some moisture may be removed due to cooling of the gas stream, if an aqueous solvent is used. When a nonaqueous solvent is used moisture is generally not permitted to condense. In any event, the gas stream leaving the scrubber still contains moisture, and in fact can be saturated with moisture, even if a nonaqueous scrubbing agent is used. Moisture is more strongly adsorbed than hydrocarbons and carbon oxides by conventional adsorbents; accordingly, unless the moisture is removed from the gas stream entering the adsorption units, it will be preferentially adsorbed onto the adsorbent, thereby significantly reducing the capacity of the adsorbent for hydrocarbon adsorption.

The problem of moisture is further aggravated when ambient air is used as a purge gas for regeneration of the beds of adsorbent. Ambient air contains moisture; thus, moisture will replace the hydrocarbon being desorbed from the adsorption beds during the purge step when the beds are purged with the air. This will further reduce the capacity of the adsorbent during the adsorption step of the following cycle. Unless an additional driving force, such as reduced pressures and/or elevated temperatures are employed in the bed regeneration procedure, water will accumulate in the beds and may render the process inoperable.

Because of their industrial importance, recycle partial oxidation processes in which problems such as those noted above are eliminated or minimized are constantly sought. The present invention provides a recycle partial oxidation process which prevents moisture from accumulating in the hydrocarbon-selective adsorbents used in hydrocarbon adsorption-based recycle partial oxidation processes.

SUMMARY OF THE INVENTION

The present invention is an improvement in a recycle process for manufacturing a petrochemical by the partial oxidation of a hydrocarbon using air in the presence of a suitable catalyst under reduced conversion conditions. The reactor effluent contains the petrochemical as the main product, water as a byproduct, and unreacted hydrocarbon. The petrochemical is removed from the reactor effluent in a petrochemical recovery unit, and hydrocarbon is adsorbed from the petrochemical unit waste gas. The invention includes as steps, purging adsorbed hydrocarbon from the adsorbent with oxygen-containing gas that has been dried by passage through a water-selective adsorbent, recycling the purged hydrocarbon-oxygen-containing gas mixture to the partial oxidation reactor and regenerating the water-selective adsorbent with hydrocarbon-depleted waste gas from the hydrocarbon adsorption unit.

A first embodiment of the invention comprises the steps:

(a) contacting in a reaction zone a hydrocarbon with oxygen-containing gas in the presence of an appropriate oxidation catalyst under conditions which produce a product gas comprising, inter alia, the petrochemical, unreacted hydrocarbon, and moisture;

(b) removing the petrochemical from the product gas in a petrochemical recovery zone, which releases a petrochemical-free gas;

(c) passing at least part of the petrochemical-free gas through a hydrocarbon-selective adsorbent, thereby adsorbing unreacted hydrocarbon onto the hydrocarbon-selective adsorbent and producing hydrocarbon-depleted waste gas;

(d) drying an oxygen-containing gas selected from air and oxygen-enriched air by subjecting the oxygen-containing gas to a temperature swing adsorption drying process in a system comprised of at least two beds of moisture-selective adsorbent which are operated out of phase and in such a manner that there is always one or more beds of adsorbent in oxygen-containing gas-drying service and always one or more beds of adsorbent undergoing regeneration;

(e) at least partially regenerating the hydrocarbon-selective adsorbent by passing the dried oxygen-containing gas therethrough, thereby producing a gaseous stream comprising desorbed hydrocarbon and oxygen-containing gas;

(f) recycling at least part of the gaseous stream comprising desorbed hydrocarbon and oxygen-containing gas to the reaction zone;

(g) at least partially regenerating the bed(s) of moisture-selective adsorbent undergoing regeneration by passing hydrocarbon-depleted waste gas from step (c) above through the bed(s).

In a second and preferred embodiment of the invention, both the petrochemical-free gas and the oxygen-containing gas are dried before passing these gases through the bed of hydrocarbon-selective adsorbent. This is accomplished by subjecting these gases to temperature swing adsorption drying processes in a system comprised of at least three beds of moisture-selective adsorbent which are operated out of phase and in such a manner that there is always one or more beds of adsorbent in petrochemical-free gas drying service, always one or more beds of adsorbent in oxygen-containing gas-drying service and always one or more beds of adsorbent being regenerated. The one or more beds of adsorbent undergoing regeneration are at least partially regenerated by passing hydrocarbon-depleted waste gas through the beds.

In a more preferred aspect of the second embodiment of the invention, the system that the temperature swing adsorption drying processes are carried out in comprises three beds of zeolite 3A.

In a more preferred aspect of the second embodiment, the one or more beds of adsorbent that are being regenerated are first heated by passing heated hydrocarbon-depleted waste gas through the bed(s) and then cooled by passing unheated hydrocarbon-depleted waste gas through the bed(s). In this aspect, the period of time that a bed of adsorbent is heated and the period of time that a bed of adsorbent is cooled are of preferably of equal duration, and the duration of each is preferably equal to one-fourth the duration of the period of time that a bed of adsorbent is in petrochemical-free gas drying service or oxygen-containing gas-drying service.

In a most preferred embodiment of the invention the drying system comprises four beds of moisture-selective adsorbent, and there is always one bed of adsorbent in petrochemical-free gas drying service, always one bed of adsorbent in oxygen-containing gas drying service, always one bed of adsorbent being heated by passing therethrough heated hydrocarbon-depleted waste gas and always one bed of adsorbent being cooled by passing therethrough unheated hydrocarbon-depleted waste gas. In a preferred aspect of this embodiment, the period of time that a bed of adsorbent is heated and the period of time that a bed of adsorbent is cooled are of equal duration, and the duration of each of these steps is equal to one-half the duration of the period of time that a bed of adsorbent is in petrochemical-free gas drying service or in oxygen-containing gas drying service. In another aspect of this embodiment, unheated hydrocarbon-depleted gas passes through a bed of adsorbent that has just completed the step of being heated, thereby cooling that bed of adsorbent and heating the hydrocarbon-depleted gas, and the heated hydrocarbon-depleted gas then passes through a bed of adsorbent that has just completed its adsorption step, thereby warming that bed of adsorbent. The warmed hydrocarbon-depleted gas is preferably further heated prior to its passing through the bed of adsorbent that has just completed its adsorption step.

In another preferred aspect of the invention, steps (c) and (d) of the first embodiment are each carried out at the same or different pressures in the range of about 1.2 to about 5 bara. In a preferred alternative of this aspect, steps (c) and (d) are carried out at substantially the same pressure, which is preferably in the range of about 1.2 to about 1.75 bara. In another preferred alternative of this aspect, steps (c) and (d) are carried out at different pressures, and between steps (c) and (d) there may be the additional steps of desorbing hydrocarbon from said hydrocarbon-selective adsorbent by depressurization and recycling said desorbed hydrocarbon to said reaction zone. In the latter alternative, step (c) is preferably carried out at a pressure in the range of about 1.2 to about 1.75 and step (d) is preferably carried out at a pressure in the range of about 1 to about 1.5 bara.

The moisture-selective adsorbent is preferably one that does not strongly adsorb gases other than moisture. The most preferred moisture selective adsorbent is zeolite 3A.

In other preferred embodiments of the invention, the oxygen-containing gas is ambient air; the hydrocarbon being oxidized is n-butane and the petrochemical product being produced is maleic anhydride; and part of the petrochemical-depleted gas stream is recycled to said reaction zone.

BRIEF DESCRIPTION OF THE DRAWINGS

The same reference numerals are used to represent the same or similar parts in the various drawings.

DETAILED DESCRIPTION OF THE INVENTION

The improvement of the invention can be applied to any partial oxidation reaction in which a gaseous hydrocarbon is reacted with an oxygen-containing gas in the presence of an appropriate catalyst to produce a gaseous product stream containing the petrochemical, unreacted hydrocarbon and moisture; the petrochemical is separated from the gaseous product stream; unreacted hydrocarbon is adsorbed from the remaining gaseous product stream by adsorption; and the separated hydrocarbon is desorbed from the bed of adsorbent and recycled to the partial oxidation reactor. Typical of such processes are those used to manufacture cyclic anhydrides, such as maleic anhydride; alkylene oxides, such as ethylene oxide; aldehydes, such as acetaldehyde; nitriles, such as acrylonitrile; and chlorinated hydrocarbons, such as vinyl chloride. The details of such partial oxidation reaction-based processes are well known and form no part of the present invention. These processes are described in detail in U.S. Pat. Nos. 5, 126,463, 5,262,547, and 5,278,319, the specifications of which are incorporated herein by reference.

The petrochemical manufacturing processes in which the subject invention is employed are those in which some or all of the oxygen-containing gas that is used in the partial oxidation reaction is introduced into the system in the hydrocarbon recovery section of the plant as a purge gas to purge unreacted hydrocarbon from the adsorbent. The oxygen-containing gas may be air or oxygen-enriched air. By oxygen-enriched air is meant air that contains more oxygen than is naturally present in air. Oxygen-enriched air can be prepared, for example, by adding oxygen to ambient air. Supplemental oxygen-containing gas may be supplied directly to the reactor, if desired. Air is the preferred oxygen-containing gas, since its is inexpensive and readily available. For ease of description, the oxygen-containing gas used in the process of the invention may frequently be referred to as air.

The invention can be better understood from the accompanying drawings. Auxiliary equipment, including valves, compressors and heat exchangers, that is unnecessary for an understanding of the invention have been omitted from the drawings to simplify discussion of the invention.

Figure 1:
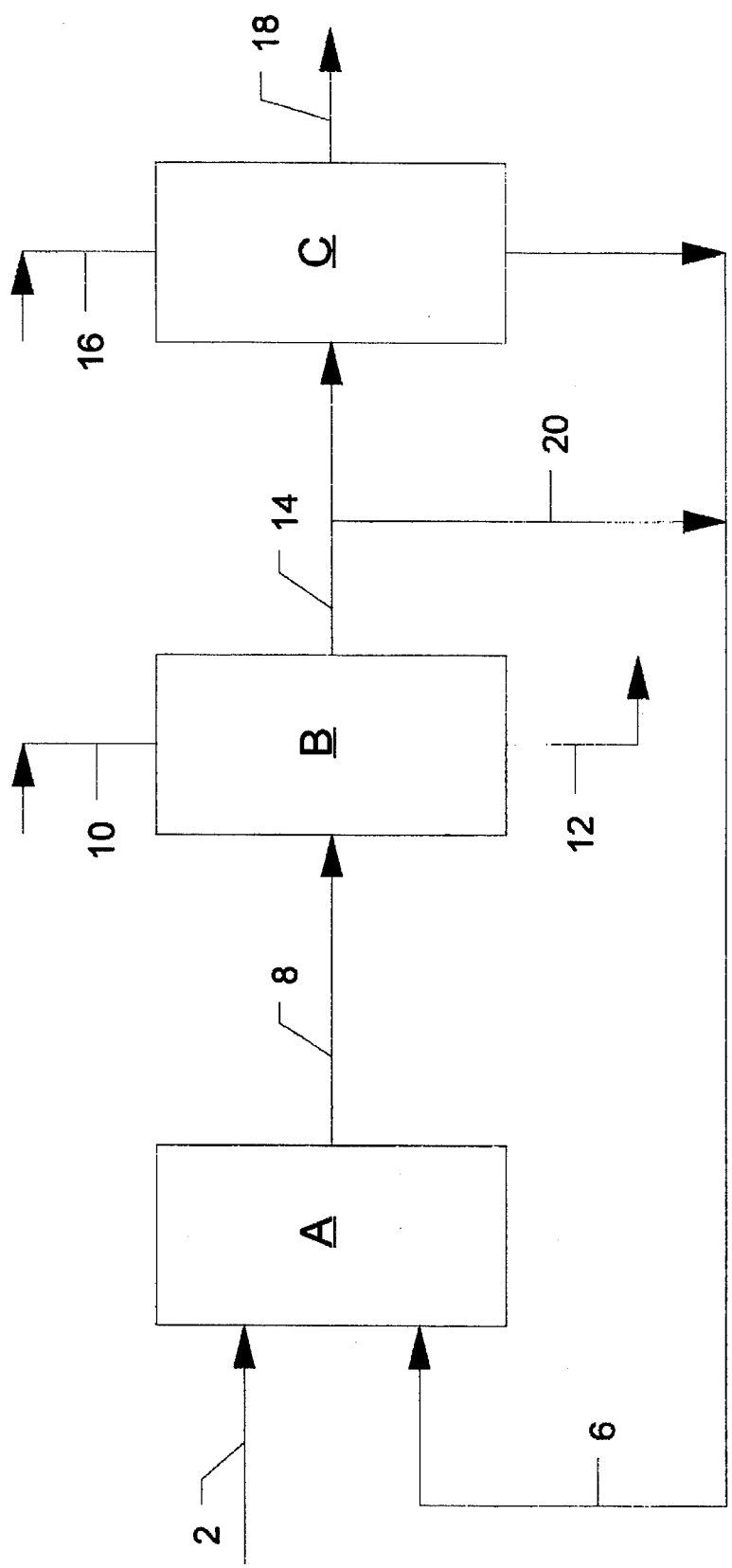
FIG. 1 illustrates, in a block diagram, a general system for carrying out the process of the invention.

Considering first FIG. 1, the system depicted therein includes, as essential equipment units, hydrocarbon partial oxidation reactor A, petrochemical product recovery unit B and separator plant C. On its inlet end, reactor A is provided with reactor inlet line 2, used for the introduction of hydrocarbons and supplemental reactants into reactor A, and hydrocarbon recycle and air supply line 6. On its outlet end, reactor A is provided with product gas discharge line 8. Reactor A may be any suitable reactor, and the design and operating details of such partial oxidation reactors are well known and form no part of the present invention.

Line 8 is connected to the petrochemical feed inlet of petrochemical product recovery unit B, which may be any unit that functions to separate petrochemical partial oxidation products from by-product gases. The design and operating details of suitable petrochemical recovery units are likewise well known and form no part of the present invention. To simplify the description of the process of the invention, petrochemical recovery unit B will be generally referred to as a scrubber. Scrubber B receives a scrubbing liquid through inlet 10 and discharges a liquid product through outlet 12. Scrubber B is also equipped with a scrubbed gas outlet 14 which serves as a petrochemical-free gas feed line to separator plant C.

Separator plant C includes a hydrocarbon adsorption system and a gas drying system for drying the petrochemical-free and the oxygen-containing gases entering separator C. Purge air supply line 16 provides purge air to separator plant C, and waste gas line 18 serves to remove waste gases from this plant. Recycle line 6 serves to return unreacted hydrocarbon and purge air to reactor A. Bypass line 20 joins line 14 to line 6.

The hydrocarbon-adsorption system of separator C generally comprises a battery of two or more substantially identical adsorption units, each packed with a hydrocarbon-selective adsorbent and operated out of phase such that one or more units are in adsorption service producing purified adsorbate, while one or more other units are undergoing regeneration to release the adsorbed hydrocarbon. Operation of the hydrocarbon adsorption system is cyclical. A partial cycle (half-cycle) occurs when one bed has undergone all of the steps in the adsorption process, and a full cycle occurs when each bed of the adsorption system has undergone a partial adsorption cycle. In the complete adsorption process full cycles are repeatedly carried out, so that the process is substantially continuous.

The hydrocarbon adsorption process used in the invention may be PSA, VSA (vacuum swing adsorption—a variation of PSA wherein the adsorption step is carried out at low pressures and the regeneration step is conducted under vacuum), CSA (concentration swing adsorption—a cyclical adsorption process conducted at any desired temperature and pressure in which a gas is first adsorbed onto an adsorbent, and the adsorbent is regenerated by flushing the adsorbent with a purge gas, usually without an intentional effort to change the pressure or temperature of the system during the cycle), or combinations of any of these.

The hydrocarbon adsorption step can be carried out at high pressures, for example pressures up to about 20 bara (bar, absolute) or higher; however, it is usually carried out at pressures not in excess of about 5 bara. In general, it is preferred to conduct the hydrocarbon adsorption step at pressures that render this step most congruous with other steps of the overall process. The scrubbed gas from scrubber B is generally available at pressures up to about 2 bara. Operating the hydrocarbon adsorption process at adsorption pressures in the range of about 1.2 to about 1.75 bara will enable the scrubbed gas stream to pass through the hydrocarbon adsorbers and the dryers that are being regenerated and to reach a downstream incinerator (or other disposal means) without the use of supplemental blowers or compressors. Accordingly, it is preferred to conduct the adsorption step at pressures in the range of about 1.2 to about 1.75 bara.

The temperature at which the hydrocarbon adsorption is carried out is not critical, and, in general, can vary from low temperatures, e.g. temperatures of about −50° C. to relatively high temperatures, for example temperatures of about 150° C. The adsorption is usually carried out at temperatures in the range of about 0° to about 100° C., and most often at temperatures in the range of about 20° to about 50° C. The adsorption is preferably carried out at the temperature which provides optimum separation and which is in harmony with other steps of the product manufacturing process, if possible. The optimum adsorption temperature of the process will depend, inter alia, upon the particular adsorbent being used, the pressure at which the process is carried out and the specific gases being separated. Those skilled in the art can easily determine which operating conditions are best suited for their purposes.

A key feature of the hydrocarbon adsorption process is the step of purging the adsorption beds with air or oxygen-enriched air. This step serves the dual purpose of purging hydrocarbon from the beds and providing some or all of the oxygen required for the partial oxidation reaction. In CSA processes, and, to a considerable extent, in PSA processes, the air purge step serves as the principal bed regeneration means. In PSA processes, the bed air purge step may occur during the countercurrent depressurization step, or subsequent thereto as a separate step, or both during and after the countercurrent depressurization.

During part or all of the hydrocarbon adsorbent regeneration step(s), dried oxygen-containing gas is passed as a purge gas through the vessel(s) that are undergoing bed regeneration. The purge gas is ideally introduced into separator C at a pressure that will be sufficient to drive the purge gas through the dryer in air drying service and the hydrocarbon adsorption vessel being regenerated and to reactor A. If the bed-purging step is conducted at superatmospheric pressure, the oxygen-containing gas is pressurized to the desired pressure by means of blower 42. The desired pressure is often the minimum pressure necessary to cause the oxygen-containing gas to flow through the system. In general, the absolute pressure during the regeneration step of PSA cycles is usually in the range of about 20 millibara to about 2 bara. Although bed regeneration can be carried out at subatmospheric pressures, it is often preferable to avoid vacuum pressures, and to conduct this step at about atmospheric pressure or above, to avoid the use of high energy-consuming vacuum generating equipment. In preferred embodiments of the invention, regeneration of the hydrocarbon adsorbers is carried out a pressures in the range of about 1 to about 1.5 bara.

The oxygen-containing gas used as a purge stream may be introduced into the system at ambient temperature or hotter. It is generally preferred, however, to use purge gas that is at ambient temperature so that there will be little or no change of temperature over the course of the adsorption-bed regeneration cycle, since the adsorption process cannot be efficiently practiced if the beds are heated during bed regeneration without recooling the beds for the next succeeding adsorption step of the process.

The hydrocarbon-selective adsorbent can be any of the well-known adsorbents that adsorb gaseous hydrocarbons more strongly than they do adsorb carbon oxides, nitrogen, oxygen, etc. Suitable adsorbents include silica gel, activated carbon, molecular sieves, such as natural zeolites, including faujasite, mordenite, erionite, etc., and synthetic zeolites, including 4A, 5A, 10X, 13X zeolites, etc. The preferred adsorbents are silica gel, activated carbon, zeolite 5A and zeolite 13X. The particular hydrocarbon-selective used in the process of the invention does not constitute a critical part of the invention.

Separator plant C also contains a battery of three or more vessels containing moisture-adsorbing gas-drying beds. The gas-drying beds are designed to be sequenced through a cycle in which there is always at least one bed in service drying the hydrocarbon-depleted gas discharged from one of vessels 30, 32 as a nonadsorbed gas stream; always at least one bed in service drying the oxygen-containing gas that is introduced into the system to purge the adsorbed hydrocarbon from the adsorbent in vessels 30 and 32, and always at least one bed of adsorbent that is undergoing bed regeneration. Each dryer vessel contains a bed of moisture-selective adsorbent, such as zeolite 3A, alumina, etc. In the most preferred embodiment of the invention, each vessel contains a bed of zeolite 3. This adsorbent is especially suitable for use in the gas drying steps of the invention because it readily adsorbs moisture from the gas streams being dried in the process, without adsorbing other components of the gas streams.

The gas dryers are usually carried out using a TSA cycle. The gases to be dried enter the dryers at temperatures and pressures that are compatible with the operations that are being carried out in the hydrocarbon adsorption units of separator C. In general the petrochemical-free gas desirably enters the dryers at a temperature in the range of about 0° to about 60° C. and preferably at a temperature in the range of about 20° to about 40° C. The air is generally introduced at ambient temperatures, e.g. 0° to about 60° C. During bed regeneration, the regeneration gas, i.e. hydrocarbon-depleted waste gas from the hydrocarbon adsorbers, is usually introduced into the dryers at low pressures, for example, pressures in the range of about 1.2 to about 2 bara. The regeneration gas is usually heated to a temperature in the range of about 150° to about 300° C., and preferably to a temperature in the range of about 200° to about 250° C. The operating conditions of the dryer units are not critical.

Figure 2:
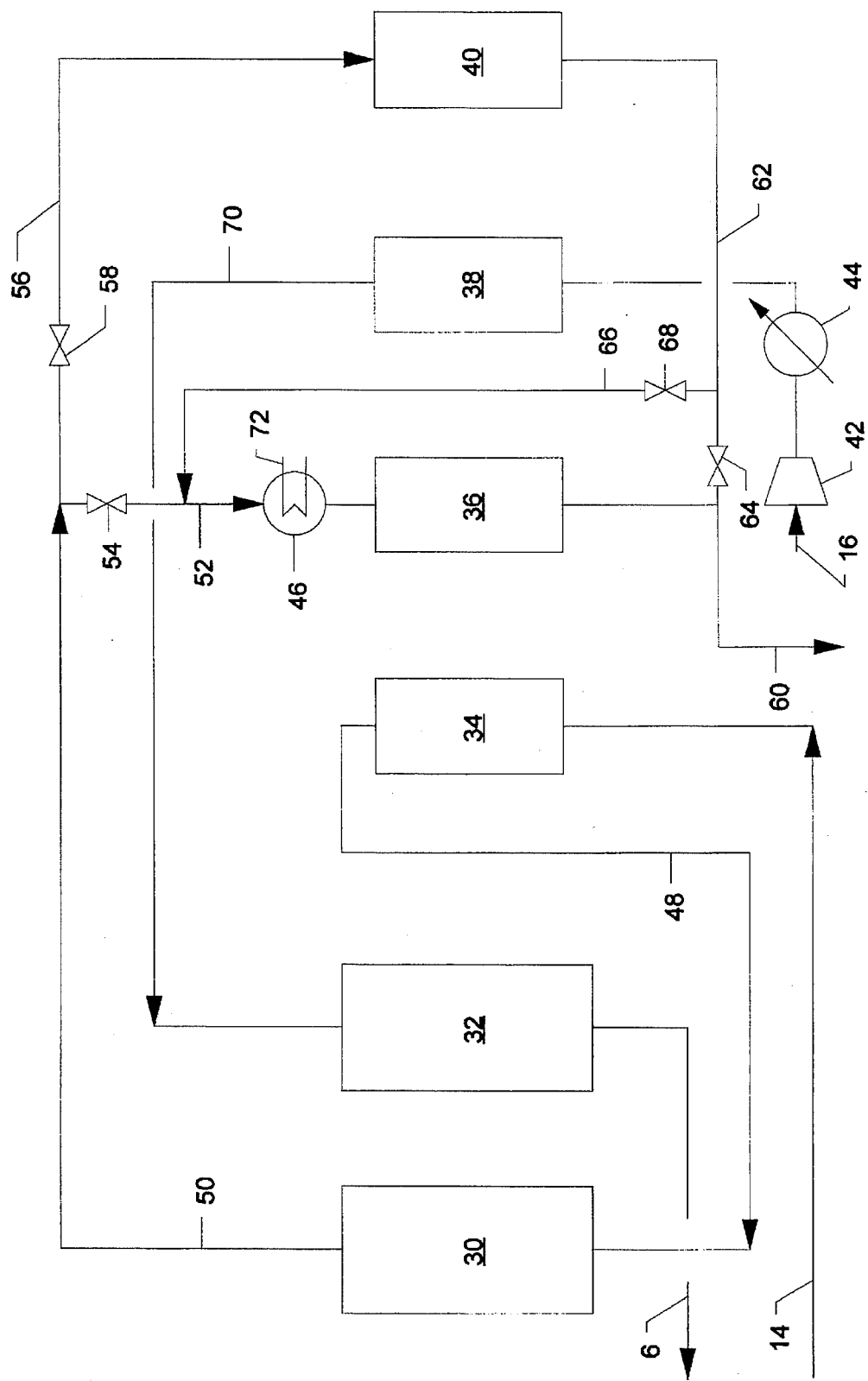
FIG. 2 illustrates, in a block diagram, a four-dryer vessel system in which preferred embodiments of the hydrocarbon recovery steps of the process of the invention can be carried out.

FIG. 2 illustrates specific details of a preferred embodiment of separator plant C. In this embodiment, the hydrocarbon adsorption system is a twin bed system comprising parallel-arranged vessels 30 and 32, each packed with one or more hydrocarbon-selective adsorbents and operated 180° out of phase. The invention will be described in detail as practiced in such an arrangement; however, the illustrated system is merely exemplary of systems in which the process of the invention can be practiced.

Figure 5:
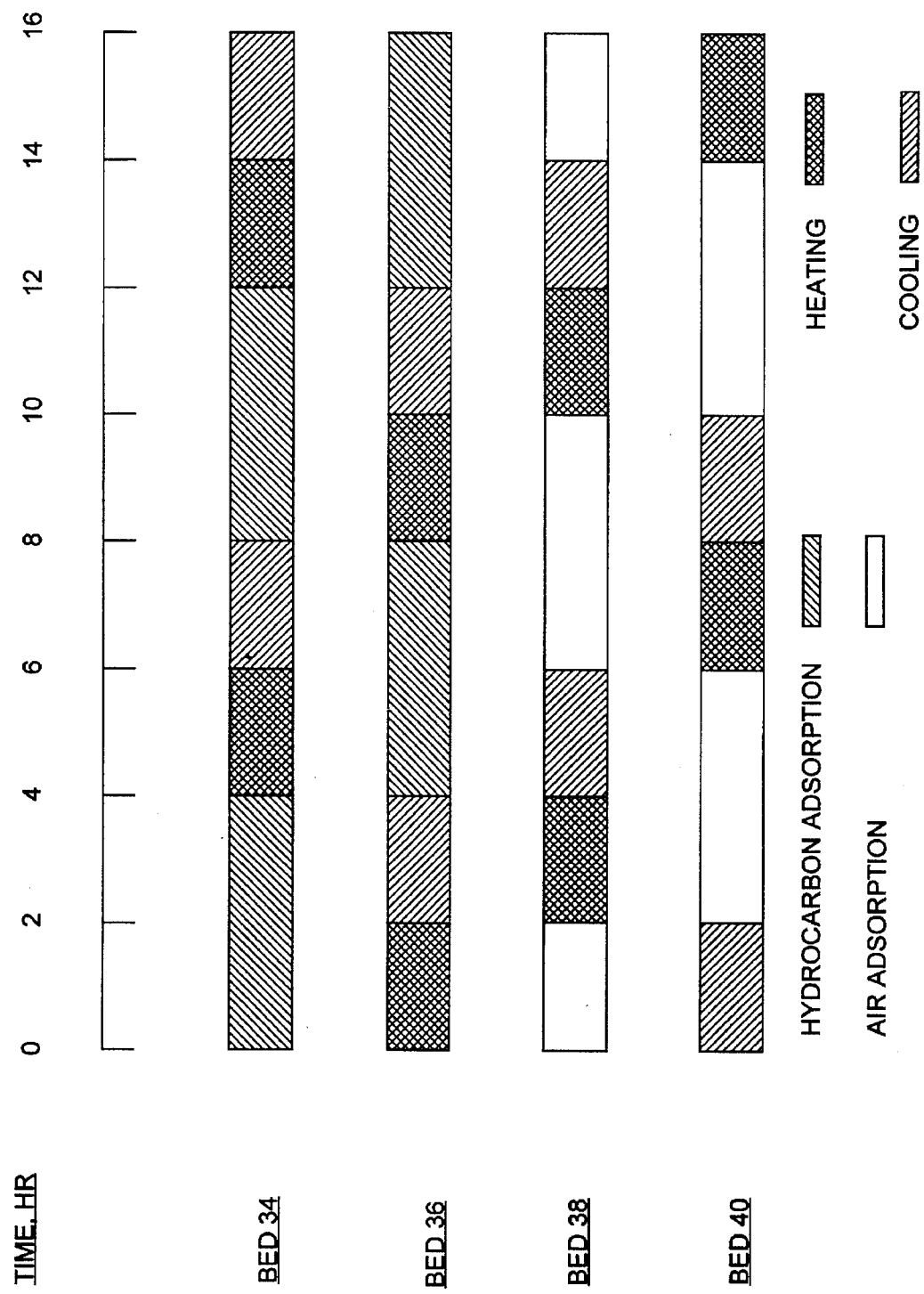
FIG. 5 is a chart showing the sequence of steps in cycles carried out in the system of FIG. 2.

The system of FIG. 2 includes a battery of four dryers, vessels 34, 36, 38 and 40. This system is designed to be sequenced through a cycle in which the bed in one of vessels 34 to 40 is always in the hydrocarbon adsorption step and another bed in one of these vessels is always in the air drying step while the beds in the other two of these four vessels are undergoing the heating and cooling steps of the bed regeneration phase of the drying cycle. In the most preferred cycle of the four bed system of FIG. 2, the bed heating and the bed cooling steps of the regeneration cycle are of equal duration and the duration of each of these steps is one-half the duration of each adsorption step. This drying cycle is most preferred because heater 46 is in continuous service; thus loss of efficiency due to cooling and reheating of the heater coils is avoided. FIG. 5 shows a preferred bed sequencing order for a four-bed gas drying system. The arrangement illustrated in FIG. 2 occurs during the first two hours of the cycle illustrated in FIG. 5. In this cycle, a bed is in the adsorption mode for 4 hours, then in the heating mode for 2 hours and finally in the cooling mode for two hours.

The system of FIG. 2 also includes purge gas supply line 16, which is provided with optional air blower 42 and optional air cooler 44. Air blower 42 is used only if it is deemed desirable or necessary to increase the pressure of air being introduced into the system. Cooler 44 is usually used to remove the heat of compression of the air passing through blower 42. Although air blower 42 and air cooler 44 are depicted as connected only to the feed inlet end of vessel 38, these units are also connected to the feed inlet ends of vessels 34, 36 and 40 through a valved manifold system. The system of FIG. 2 likewise includes heater 46, which is depicted as attached only to the nonadsorbed gas outlet end of vessel 36; however, it is likewise connected to the nonadsorbed gas outlets of vessels 34, 38 and 40 through a valved manifold system.

Line 14 connects the scrubbed gas outlet of scrubber B with the feed inlet end of dryer vessel 34 and the nonadsorbed gas outlet of dryer 34 is connected to the feed gas inlet of vessel 30 through line 48. Line 50 conducts the nonadsorbed waste gas stream from adsorber 30. Line 50 is connected to line 52, which is fitted with valve 54 and heater 46, and to line 56, which is connected to the outlet end of vessel 40. Line 56 is equipped with valve 58. Line 52 is connected to the outlet end of vessel 36. On its inlet end, vessel 36 is connected to waste gas discharge line 60. The inlet end of vessel 40 is also connected to waste gas discharge line 60 through line 62. Line 62 is fitted with valve 64. Gas in line 62 can flow to the inlet end of heater 46 via line 66. Line 66 is fitted with valve 68.

Purge air supply line 16, which is provided with air compressor 42 and air cooler 44, joins the inlet end of vessel 38. The outlet end of vessel 38 is connected to the outlet end of vessel 32 via line 70. The inlet end of vessel 32 is connected to recycle line 6, which, as mentioned above, is connected to reactor A. Heater 46 is provided with heating coil 72.

The various pipelines are illustrated in FIG. 2 as connected to certain hydrocarbon adsorbing and certain drying vessels, however it should be understood that they are similarly connected to each of the vessels of a battery. Operation of the system of FIG. 2 will be described in detail with adsorption vessels 30 and 32 in the adsorption and regeneration modes, respectively, vessel 34 in hydrocarbon feed drying service, vessel 36 being regenerated with hot gas, vessel 38 in air drying service and vessel 40 being cooled for adsorption service.

Figure 3:
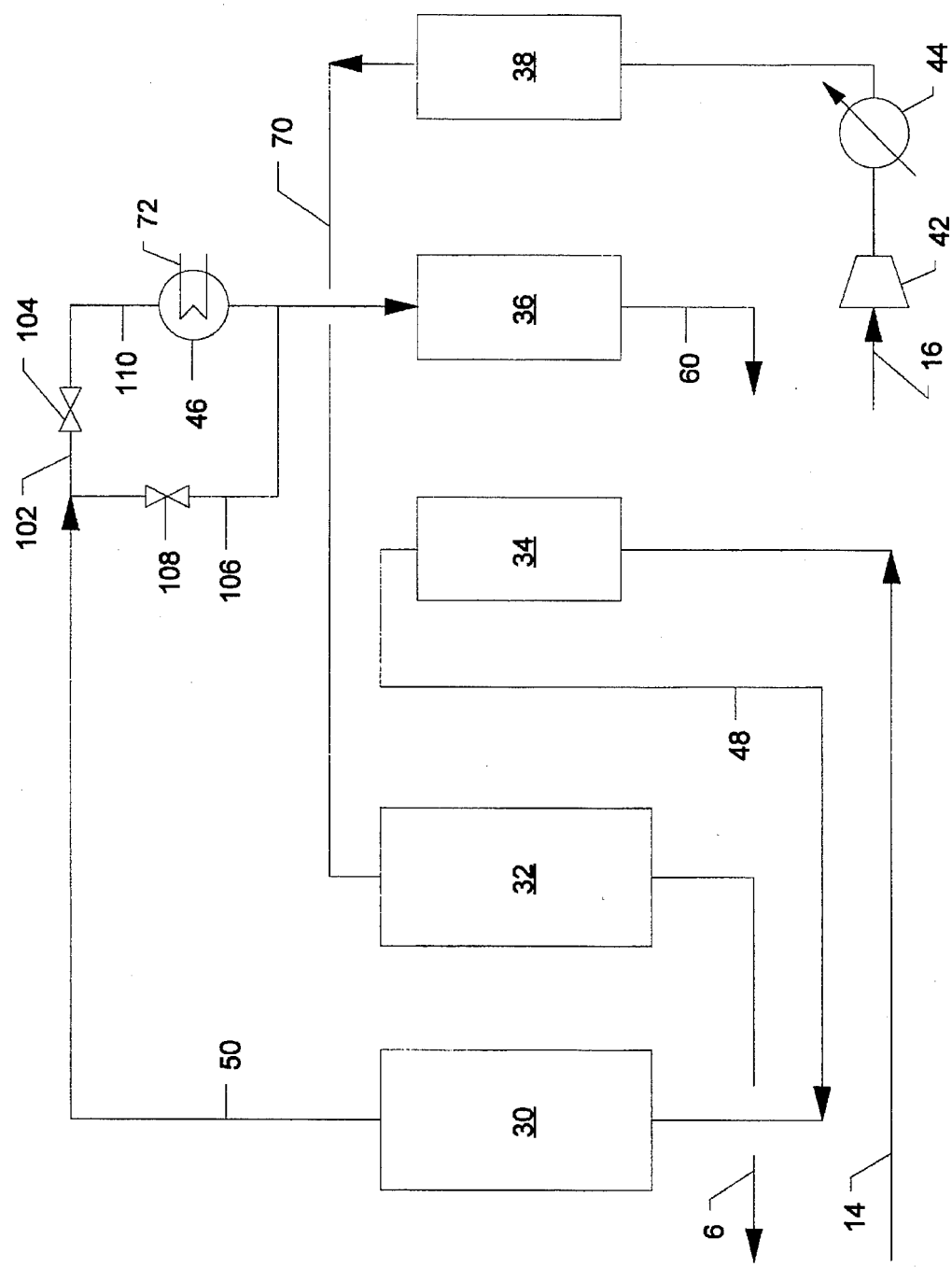
FIG. 3 illustrates, in a block diagram, a three-dryer vessel version of the system of FIG. 2.

FIG. 3 illustrates a variation of the system of FIG. 2. In the FIG. 3 system, three drying vessels are used rather than the four vessels shown in FIG. 2. As was the case in the system of FIG. 2, each of vessels 34, 36 and 38 of FIG. 3 is packed with a moisture-selective adsorbent. Line 50 connects the outlet end of vessel 30 with lines 102 and 106, which are provided with valves 104 and 108, respectively. Line 102 passes through heater 46 and is joined to the nonadsorbed outlet end of vessel 36. Line 106 joins line 110 between heater 46 and vessel 36.

Figure 6:
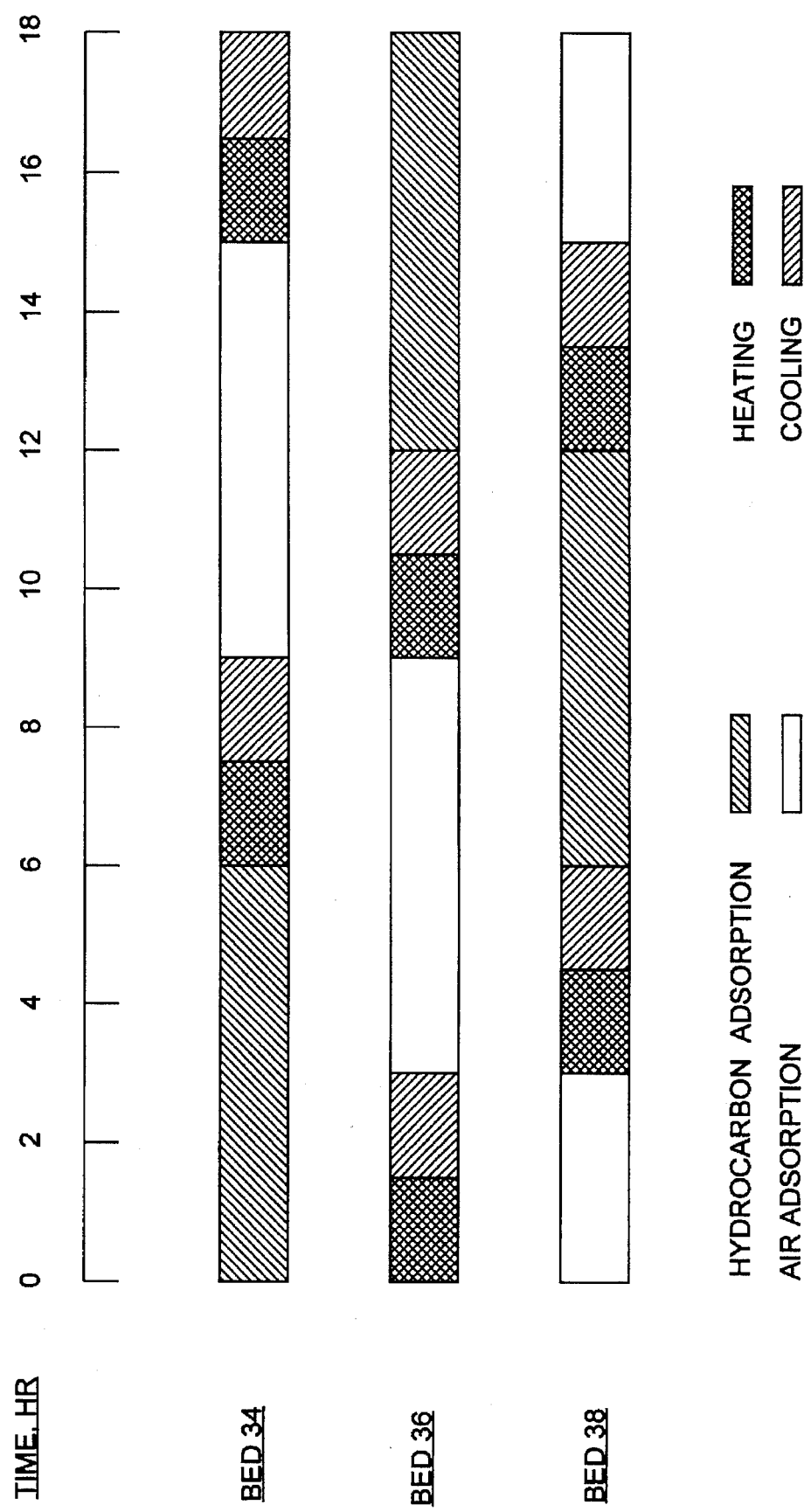
FIG. 6 is a chart showing the sequence of steps in cycles carried out in the system of FIG. 3.

The system of FIG. 3 is operated using a cycle in which there is always one bed in hydrocarbon adsorption service, one bed in air adsorption service and one bed being regenerated. In the operating cycle for the FIG. 3 system, the bed heating and bed cooling steps are of equal duration, and the duration of each is one-fourth the duration of the adsorption step. A typical cycle for the FIG. 3 system is shown in FIG. 6. Note that in the FIG. 6 cycle, the duration of the adsorption steps is six hours and the duration of the bed heating and cooling steps is one and one-half hours. The arrangement shown in FIG. 3 is in effect during the first three hours of the cycle shown in the FIG. 6 chart. During this period, the bed in vessel 34 is in hydrocarbon adsorption service, the bed in vessel 36 is undergoing the two-step regeneration procedure, and the bed in vessel 38 is in air drying service. Although the various pipelines are shown in FIG. 3 as connected to certain vessels of a battery, they are connected to each vessel of the battery.

Figure 4:
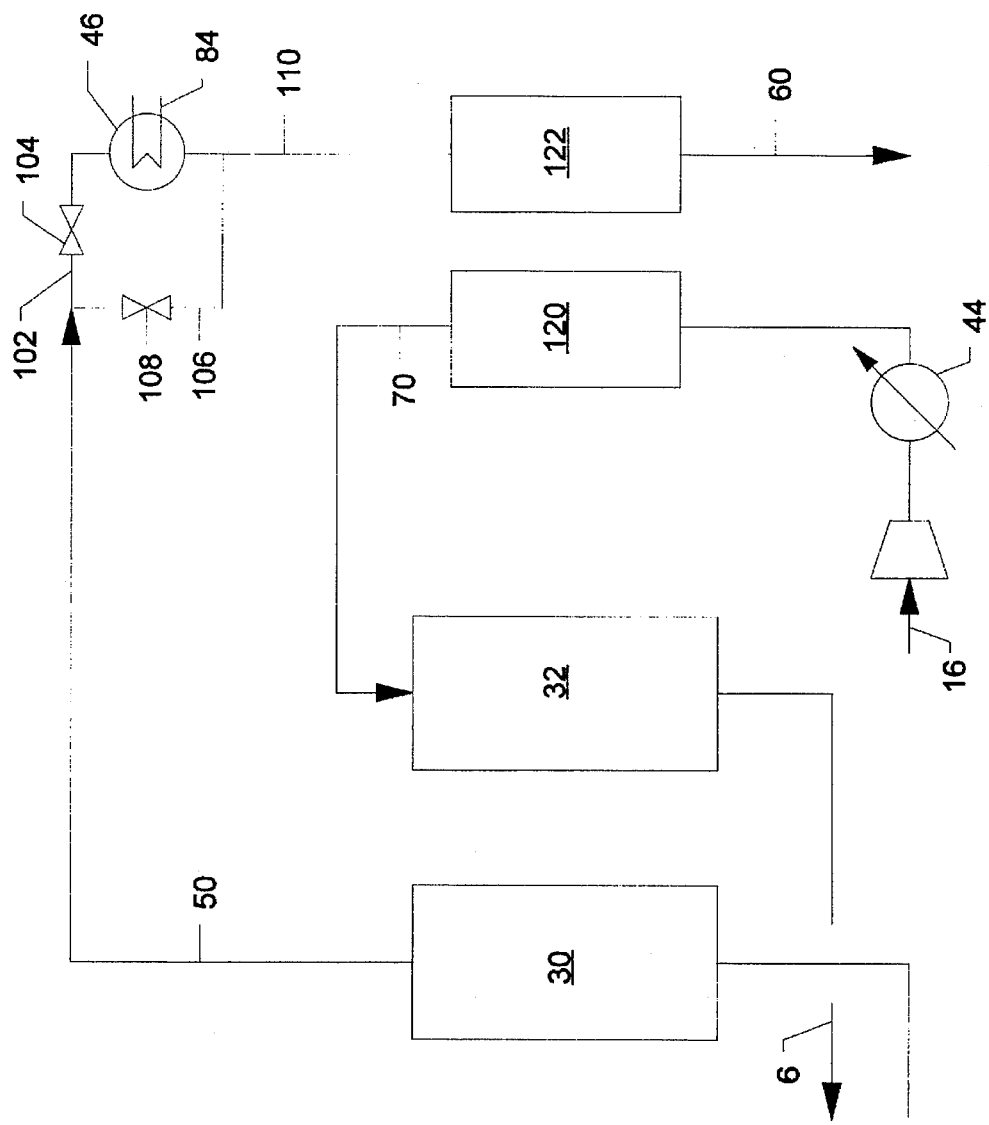
FIG. 4 illustrates, in a block diagram, another modified version of the system of FIG. 2.

FIG. 4 illustrates a variation of the system of FIG. 2 in which only the oxygen-containing gas entering the system is dried before introduction into adsorption vessels 30, 32. In other words, the petrochemical-free gas is not dried before being introduced into these vessels. In the FIG. 4 system, vessels 120 and 122 are packed with moisture-selective adsorbent, and as in the other embodiments, these vessels are operated on TSA cycles.

As shown in FIG. 4, vessel 120 is connected on its inlet end to air supply line 16 and on its nonadsorbed gas outlet end to line 70. Line 70, as in the other embodiments, is connected to the nonadsorbed gas outlet end of vessel 32. It is understood, of course that vessels 120 and 122 are designed to be operated alternately; accordingly, each of these vessels are provided with the piping connections, etc. illustrated in FIG. 4.

In carrying out the process of the invention, a gaseous hydrocarbon and an oxygen-containing gas are introduced into reactor A via feed lines 2 and 6 respectively. The feed gases entering reactor A contact the catalyst contained therein and react to form the desired petrochemical product. The product gas stream leaving reactor A contains, in addition to the desired petrochemical, carbon dioxide, carbon monoxide and water as by-products. The product stream generally also contains unreacted hydrocarbon, oxygen and nitrogen, and may contain small amounts of other by-products, impurity gases and nonreactive hydrocarbons, as well. In the embodiment illustrated in FIG. 1, the product gas stream leaves reactor A via line 8 and enters petrochemical product scrubber B.

As the product gas stream passes through scrubber B it is intimately contacted with a solvent for the petrochemical product, which enters scrubber B through line 10. The solvent dissolves substantially all of the petrochemical product out of the product gas stream. The petrochemical product-containing solution leaves scrubber B via line 12 and is usually further treated to recover the petrochemical product. A gaseous stream, now substantially petrochemical-free, leaves unit B through line 14. Part or all of this gas stream next enters separator plant C through line 14. If desired, a portion of this stream may be recycled directly back to reactor A through line 18.

Separator C serves to recover unreacted hydrocarbon from the scrubbed gas stream. In the most preferred embodiment, illustrated in FIG. 2, this is accomplished by passing the scrubbed gas first through one of dryers 34 to 40, wherein moisture is removed from the scrubbed gas, and then through one of adsorption vessels 30 and 32, wherein unreacted hydrocarbon is removed from the dried scrubbed gas. In FIG. 2, the scrubbed gas is depicted as passing first through dryer 34 and then through adsorption vessel 30.

During part of the dryer bed regeneration step the bed regeneration gas is heated in heater 46 generally to a temperature in the range of about 50° to about 300 °C., and preferably to a temperature in the range of about 100° to about 250° C., as noted above. If desired, the dryer beds can be heated during bed regeneration by supplemental heaters (not shown), but the heat imparted to the gas passing through heater 46 is generally sufficient to adequately regenerate a dryer bed without supplemental heating.

The system illustrated in FIG. 2 can be operated in several embodiments. In the first and most preferred embodiment, valves 58 and 68 are open and all other valves in the FIG.

2 system are closed. In this embodiment, moist petrochemical-free gas flows through line 14 and dryer 34. As the gas passes through dryer 34, moisture is adsorbed from the gas. Substantially dry petrochemical-free gas passes out of dryer 34 through line 48 and enters adsorption vessel 30, wherein hydrocarbons present in the gas are adsorbed by the hydrocarbon-selective adsorbent. Substantially dry, hydrocarbon-lean waste gas passes out of vessel 30 and flows through line 50, open valve 58 and line 56, and enters dryer vessel 40, which has just finished its heat regeneration step. The relatively cool waste gas passes through the hot adsorbent in vessel 40 and is heated as it cools adsorbent in this vessel. The warmed waste gas leaves vessel 40 via line 62, passes through line 66, open valve 68, line 5 and enters heater 46. Heater 46 is heated by any suitable means, such as by the passage of steam through heating coil 72. The hot waste gas exiting heater 46 next passes countercurrently through dryer vessel 36, thereby driving moisture from the bed in this vessel. The waste gas then flows out of vessel 36 through its inlet end, passes out of separator plant C through line 60 and is disposed of by any suitable means, such as by incineration.

While the beds in vessels 36 and 40 are being regenerated ambient air is drawn into line 16 by means of blower 42. Blower 42 pressurizes the ambient air sufficiently to drive it through the bed in dryer 38 and the bed of hydrocarbon-selective adsorbent that is currently in adsorption service. The air, which is heated by blower 42, can be cooled, if it is deemed necessary or desirable, by passage through optional air cooler 44. The air then passes through dryer 38, where moisture is adsorbed from the air, and the dried air passes through line 70 to vessel 32. When hydrocarbon-adsorption vessels 30 and 32 are are operated on PSA cycles and dryers 34–40 are operated on much longer TSA cycles, it is likely that dryer 38 will supply dried air to vessels 30 and 32 during more than one cycle of the latter beds. As the dried air passes countercurrently through vessel 32 it purges adsorbed hydrocarbon from this vessel. The mixture of desorbed hydrocarbon and purge air leaves vessel 32 through its inlet end and flows through line 6 to reactor A.

The above-described embodiment is most preferred because it requires less waste gas for the bed regenerating operations since the same gas stream is used to cool one dryer and heat another. Furthermore, the gas passing through the bed being cooled is partially heated in the cooling process; thus, less heat is required to raise this gas to the desired drying temperature.

In a second embodiment of the FIG. 2 arrangement, valves 54, 58 and 64 are open and all other valves are closed. In this embodiment, part of the waste gas leaving vessel 30 is heated in heater 46 and the heated gas is used to purge the bed in dryer 36; and the remainder flows through valve 58 and line 56 and is used to cool the bed in dryer 40. The gas passing through bed 36 exits this bed through its inlet end and flows through line 60 to downstream disposal. The gas passing through dryer 40 passes through line 62 and valve 64, and joins the gas exiting dryer 36. In this embodiment, air entering the system through line 16 flows through dryer 38 and to vessel 32, as before. This embodiment is less desirable than the first embodiment, since it requires a larger quantity of waste gas than is required in the first embodiment, and no use is made of the heat gained by the gas flowing through dryer 40 during the adsorbent cooling step.

The FIG. 3 system likewise has a number of operating embodiments. In the most preferred embodiment, the adsorption beds in vessels 34, 36 and 38 are regenerated by sequentially passing heated and unheated hydrocarbon-depleted waste gas through the beds. Bed 36 is regenerated during the first three hours of the time schedule of FIG. 6. For the first one and one-half hours of this period, valve 104 is open and all other valves shown in FIG. 3 are closed. Petrochemical-free gas from scrubber 13 enters the FIG. 3 system through line 14, is dried in vessel 34 and passes through vessel 30, where hydrocarbons are adsorbed from the gas. The hydrocarbon—depleted gas then passes through lines 50 and 102, open valve 104 and line 110, and enters heater 46, in which it is heated. The heated hydrocarbon-depleted gas flows through vessel 36 and desorbs moisture from the bed in this vessel, and the waste gas-moisture mixture leaves the system through line 60 and flows to downstream disposal. Meanwhile, air is drawn into the FIG. 3 system by blower 42, passes through cooler 44 and is dried in vessel 38. The dried air then passes through line 70 and enters vessel 32 and desorbs hydrocarbon from the bed in this vessel. The desorbed hydrocarbon-air mixture flows to reactor A through line 6.

During the next one and one-half hours of the FIG. 3 cycle (hours 1.5 to 3), valve 108 is open and all other valves are closed, and unheated hydrocarbon-depleted waste gas passes through lines 106 and 110 and flows through vessel 36. The unheated waste gas cools the bed in vessel 36 and desorbs additional moisture from the bed. The waste gas-moisture mixture exits vessel 36 through line 60 and flows to downstream disposal. During this period air continues to flow through dryer 38, line 70 and vessel 32, thereby further regenerating the bed in vessel 32.

In operation of the FIG. 4 system, undried petrochemical-free gas entering the system through line 14 passes through vessel 30, where moisture and hydrocarbon are adsorbed therefrom. The dried and hydrocarbon-depleted gas leaving vessel 30 through line 50 passes through line 102 and valve 104, when vessel 122 is in the heating step of regeneration, and through line 106 and valve 108, when the adsorbent in vessel 122 is being cooled. The waste gas leaves vessel 36 through line 60 and is sent to downstream disposal, as in the other embodiments of the invention.

While vessel 30 is in adsorption service, the adsorbent in vessel 32 is purged with air from vessel 120. In this part of the operation, air is drawn into the system by means of blower 42, is cooled in cooler 44 (if necessary) and passes through adsorber 120, wherein moisture is removed from the air. The dry air flows out of vessel 120 through line 70 and passes countercurrently through vessel 32, thereby desorbing moisture and hydrocarbon from the bed in this vessel. The mixture of hydrocarbon, moisture and air passes out of vessel 32 through line 6 and flows to reactor A.

During at least part of the period that vessel 120 is in adsorption service, vessel 122 is being regenerated for its next adsorption shift. During at least part of the regeneration period valve 104 is open and dry hydrocarbon-depleted waste gas air flows through line 102, is heated in heater 46, and flows countercurrently through the bed in vessel 122, thereby purging moisture from the bed. The purge gas-moisture mixture flows out of vessel 122 through line 60 and is sent to downstream disposal. Upon completion of the bed heating period of the regeneration step, valve 108 is opened and valve 104 is closed. Unheated dry hydrocarbon-depleted waste gas then flows countercurrently through vessel 122 and cools the bed therein for its next adsorption assignment.

It will be appreciated that it is within the scope of the present invention to utilize conventional equipment to monitor and automatically regulate the flow of gases within the system so that it can be fully automated to run continuously in an efficient manner.

The invention is further illustrated by the following examples in which percentages, ratios, and parts, including parts per million (ppm), are on a volume basis, unless otherwise indicated. The experiments described in the examples were carried out in a pair of laboratory adsorption vessels that were 3Δ in diameter and 22Δ high with inert packing at each end. The feed gas and desorbed gas streams were monitored and analyzed for composition using a Shimadzu gas chromatograph with a Thermal Conductivity Detector. The carbon dioxide recovery was calculated based on the indicated measurements of the streams.

EXAMPLE I

In this example the laboratory adsorption vessels were continuously operated alternately and out of phase on an adsorption/purge cycle with a 2 minute full cycle time at a temperature of about 23°–24° C. Each vessel was packed with about 1200 grams of silica gel adsorbent, size 3×9 mesh, sold by Davison Company under the designation Grade 41. The average composition of the feed gas over the life of the experiment was: 5.4% carbon dioxide, and the balance nitrogen. The feed flow rate was about 15 slpm (standard liters per minute). Dry nitrogen was used as the purge gas at a flow rate of about 15 slpm, i.e. the purge/feed volume ratio was about 1. The feed gas was saturated with moisture by bubbling the gas through water at room temperature. During the adsorption step the bed pressure was maintained at about 25.5 psia (pounds per square inch, absolute). During bed regeneration a bed pressure of about 17.5 psia was maintained. The test run was conducted for a period of 12 days, during which period the carbon dioxide recovered in the desorbed gas remained constant at about 80%.

EXAMPLE II

The procedure of Example I was repeated except that the composition of the feed gas was 1.9% butane, 7% carbon dioxide and the balance nitrogen, both the feed gas and the purge gas were dry, the feed gas flow rate was maintained at about 20 slpm, the purge/feed ratio was maintained at about 1, the bed pressure was maintained within the range of about 20.5 to 21.5 psia and the bed temperature was maintained in the range of about 40° to 47° C. The test run was conducted for a period of 7 days, during which period the butane recovery remained in the range of about 91 to 92% and the carbon dioxide recovery remained in the range of about 57 to 58%.

EXAMPLE III COMPARATIVE)

The procedure of Example I was repeated except that both the feed and the nitrogen purge gas were saturated with moisture, and both the adsorption pressure and the regeneration pressure were maintained at about 20 psia during the run. The run was carried out for a period of eleven days. The percentage of carbon dioxide recovered on the first, fourth, sixth, eighth and eleventh days was 60%, 45%, 41%, 35% and 15%, respectively.

The above examples illustrate the benefit of the invention. The feed gas used in Examples I and III was a mixture of nitrogen and carbon dioxide, and the feed gas used in Example II was a mixture of nitrogen, butane and carbon dioxide. These gas mixtures simulate the waste gas stream from a partial oxidation reactor. During the adsorption process step most of the nirogen passes through the adsorbent as nonadsorbed gas. In Examples I and III, most of the carbon dioxide is adsorbed and recovered as a carbon dioxide-enriched desorbed gas product and in Example II most of the butane and carbon dioxide is adsorbed and recovered as a butane- and carbon dioxide-enriched desorbed gas product. The experiment of Example I was conducted under PSA conditions using a pressure swing of about 8 psi. In this experiment, the feed gas was saturated with moisture but the purge gas was dry. The experiment was successfully carried out over a period of 12 days. The experiment of Example II was carried out substantially under CSA conditions using a purge gas to feed gas ratio of about 1. This experiment was likewise successfully carried out for period of 7 days. In Example III, the experiment was carried out under CSA conditions using a wet feed gas and a wet purge gas. A feed/purge gas ratio of 1 was maintained during the experiment. The carbon dioxide recovery in the Example III experiment fell off rapidly and continued to decline until it was only 15% on the last day of the run.

Experiment 1 illustrates that when the purge gas stream is dry, carbon dioxide can be continuously recovered from a wet gas under PSA conditions Example II illustrates that when both the feed gas and the purge gas are dry, butane and carbon dioxide can be continuously recovered from the feed gas when the purge/feed ratio is about 1. Example III illustrates that when both the feed gas and the purge gas are wet, carbon dioxide cannot be continuously recovered from a wet feed gas when the purge/feed ratio is about 1.

When both the purge gas and the feed gas are dried prior to the hydrocarbon adsorption process, the process can be conducted under CSA conditions at considerably lower purge gas/feed gas ratios than shown in the examples. The purge/feed ratio is then limited only by the oxygen requirement of the partial oxidation reaction.

Although the invention has been described with particular reference to a specific equipment configuration and to specific experiments, these are merely exemplary of the invention, and variations are contemplated. The scope of the invention is limited only by the breadth of the appended claims.

What is claimed is:

1. In a method of producing a petrochemical comprising:
   (a) contacting a hydrocarbon with an oxygen-containing gas selected from air and oxygen-enriched air in a reaction zone in the presence of an appropriate oxidation catalyst under conditions which produce a product gas comprising said petrochemical, unreacted hydrocarbon, and moisture;
   (b) removing said petrochemical from said product gas in a petrochemical recovery zone, thereby producing petrochemical-free gas;
   (c) passing at least part of said petrochemical-free gas through a hydrocarbon-selective adsorbent, thereby adsorbing unreacted hydrocarbon onto said hydrocarbon-selective adsorbent and producing hydrocarbon-depleted waste gas;
   (d) at least partially regenerating said hydrocarbon-selective adsorbent by passing oxygen-containing gas therethrough, thereby producing a gaseous stream comprising desorbed hydrocarbon and oxygen-containing gas; and
   (e) recycling at least part of said gaseous stream to said reaction zone; the improvement comprising, prior to passing said oxygen-containing gas through said bed of hydrocarbon-selective adsorbent, subjecting the oxygen-containing gas to a temperature swing adsorption drying process in a system comprised of at least two beds of moisture-selective adsorbent which are operated out of phase and in such a manner that there is always at least one bed of adsorbent in oxygen-containing gas-drying service and at least one bed of adsorbent undergoing regeneration; said at least one bed of adsorbent undergoing regeneration being at least partially regenerated by passing therethrough said hydrocarbon-depleted waste gas.

2. The improved method of claim 1, wherein said improvement comprises, prior to passing said petrochemical-free gas and said oxygen-containing gas through said bed of hydrocarbon-selective adsorbent, subjecting these gases to temperature swing adsorption drying processes in a system comprised of at least three beds of moisture-selective adsorbent which are operated out of phase and in such a manner that there is always at least one bed of adsorbent in petrochemical-free gas drying service, at least one bed of adsorbent in oxygen-containing gas-drying service and at least one bed of adsorbent undergoing regeneration; said at least one bed of adsorbent undergoing regeneration being at least partially regenerated by passing therethrough said hydrocarbon-depleted waste gas.

3. The improved method of claim 2, wherein said system comprises three beds of zeolite 3A.

4. The improved method of claim 3, wherein said at least one bed of adsorbent being regenerated is first heated by passing therethrough heated hydrocarbon-depleted waste gas and then cooled by passing therethrough unheated hydrocarbon-depleted waste gas.

5. The improved method of claim 4, wherein the period of time that a bed of adsorbent is heated and the period of time that a bed of adsorbent is cooled are of equal duration, and the duration of each is equal to one-fourth the duration of the period of time that a bed of adsorbent is in petrochemical-free gas drying service or oxygen-containing gas-drying service.

6. The improved method of claim 1, wherein said system comprises four beds of moisture-selective adsorbent, and there is always: one bed of adsorbent in petrochemical-free gas drying service, one bed of adsorbent in oxygen-containing gas drying service, one bed of adsorbent being heated by passing therethrough heated hydrocarbon-depleted waste gas and one bed of adsorbent being cooled by passing therethrough unheated hydrocarbon-depleted waste gas.

7. The improved method of claim 6 wherein the period of time that a bed of adsorbent is heated and the period of time that a bed of adsorbent is cooled are of equal duration, and the duration of each is equal to one-half the duration of the period of time that a bed of adsorbent is in petrochemical-free gas drying service or in oxygen-containing gas drying service.

8. The improved method of claim 6, wherein unheated hydrocarbon-depleted gas passes through a bed of adsorbent that has just completed the step of being heated, thereby cooling that bed of adsorbent and heating the hydrocarbon-depleted gas, and the heated hydrocarbon-depleted gas then passes through a bed of adsorbent that has just completed its adsorption step, thereby heating that bed of adsorbent.

9. The improved method of claim 8, wherein the heated hydrocarbon-depleted gas is further heated prior to its passing through the bed of adsorbent that has just completed its adsorption step.

10. The improved method of any one of claims 1, 2 or 6, wherein steps (c) and (d) are each carried out at the same or different pressures in the range of about 1.2 to about 5 bara.

11. The improved method of claim 10, wherein steps (c) and (d) are carried out at substantially the same pressure.

12. The improved method of claim 11, wherein said pressure is in the range of about 1.2 to about 1.75 bara.

13. The improved method of claim 10, wherein steps (c) and (d) are carried out at different pressures.

14. The improved method of claim 13, further comprising between steps (c) and (d) the additional steps of desorbing hydrocarbon from said hydrocarbon-selective adsorbent by depressurization and recycling said desorbed hydrocarbon to said reaction zone.

15. The improved method of any one of claims 1, 2 or 6, wherein step (c) is carried out at a pressure in the range of about 1.2 to about 1.75 and step (d) is carried out at a pressure in the range of about 1 to about 1.5 bara.

16. The improved method of any one of claims 1,2 or 6, wherein said moisture-selective adsorbent is zeolite 3A.

17. The improved method of any one of claims 1, 2 or 6, wherein said oxygen-containing gas is ambient air.

18. The improved method of claim 1, wherein said hydrocarbon is n-butane and said petrochemical product is maleic anhydride.

19. The improved method of claim 1, wherein part of said petrochemical-free gas stream is recycled to said reaction zone.

* * * * *